United States Patent
Alvarez

(10) Patent No.: US 10,799,269 B2
(45) Date of Patent: Oct. 13, 2020

(54) TRANSFER ASSEMBLY

(71) Applicant: Carlos Navarro Alvarez, Estado de México (MX)

(72) Inventor: Carlos Navarro Alvarez, Estado de México (MX)

(*) Notice: Subject to any disclaimer, the term of this patent is extended or adjusted under 35 U.S.C. 154(b) by 195 days.

(21) Appl. No.: 16/132,435

(22) Filed: Sep. 16, 2018

(65) Prior Publication Data
US 2019/0083135 A1 Mar. 21, 2019

Related U.S. Application Data

(60) Provisional application No. 62/560,104, filed on Sep. 18, 2017.

(51) Int. Cl.
| | |
|---|---|
| *A61B 17/435* | (2006.01) |
| *A61M 25/00* | (2006.01) |
| *A61M 25/10* | (2013.01) |
| *A61M 31/00* | (2006.01) |
| *A61B 90/00* | (2016.01) |

(Continued)

(52) U.S. Cl.
CPC ....... *A61B 17/435* (2013.01); *A61M 25/0075* (2013.01); *A61B 90/03* (2016.02); *A61B 2017/00477* (2013.01); *A61B 2017/4225* (2013.01); *A61B 2090/036* (2016.02); *A61B 2090/062* (2016.02); *A61M 25/003* (2013.01); *A61M 25/0054* (2013.01); *A61M 25/1002* (2013.01); *A61M 31/002* (2013.01); *A61M 2039/1033* (2013.01); *A61M 2202/0007* (2013.01); *A61M 2202/04* (2013.01); *A61M 2210/1425* (2013.01); *A61M 2210/1433* (2013.01)

(58) Field of Classification Search
CPC .... A61B 17/42–48; A61B 2017/00477; A61B 2017/4225; A61B 2090/036; A61B 2090/062; A61B 90/03; A61M 2210/1433; A61M 25/003; A61M 25/0054; A61M 25/0075; A61M 25/1002; A61M 2039/1033; A61M 2202/0007; A61M 2202/04; A61M 2210/1425; A61M 31/002
See application file for complete search history.

(56) References Cited

U.S. PATENT DOCUMENTS

| | | | |
|---|---|---|---|
| 5,935,098 A | * | 8/1999 | Blaisdell ................... A61F 6/18 604/103.01 |
| 2008/0039864 A1 | * | 2/2008 | Feuer ................ A61B 17/4241 606/119 |

(Continued)

FOREIGN PATENT DOCUMENTS

| | | | | |
|---|---|---|---|---|
| WO | WO-0132111 A1 | * | 5/2001 | ............. A61B 17/42 |
| WO | 2010118325 A2 | | 10/2010 | |

(Continued)

*Primary Examiner* — Catherine B Kuhlman
(74) *Attorney, Agent, or Firm* — Lawrence N. Ginsberg

(57) ABSTRACT

A sterile liquid transfer assembly for use with a catheter assembly. The sterile liquid transfer assembly includes a protective element and a carrier element. The protective element includes a pliable, hollow protective valve member having a pivot cutaway portion. A tubular member of the protective element depends from a surface of the hollow protective valve member. The protective valve member is configured to define a stop for limiting the insertion of the tubular member in a canal of a patient.

12 Claims, 8 Drawing Sheets

(51) Int. Cl.
*A61B 17/00* (2006.01)
*A61B 17/42* (2006.01)
*A61M 39/10* (2006.01)

(56) References Cited

U.S. PATENT DOCUMENTS

| | | | |
|---|---|---|---|
| 2008/0109010 A1* | 5/2008 | Feuer | A61B 17/4241 606/119 |
| 2009/0137970 A1* | 5/2009 | George | A61B 17/4241 604/271 |
| 2013/0165744 A1 | 6/2013 | Carson et al. | |
| 2014/0378754 A1 | 12/2014 | Buster et al. | |
| 2019/0282271 A1* | 9/2019 | Plessala | A61M 25/01 |

FOREIGN PATENT DOCUMENTS

| | | |
|---|---|---|
| WO | 2014140217 A1 | 9/2014 |
| WO | 2016144316 A1 | 9/2016 |

\* cited by examiner

TRANSFER ASSEMBLY

CROSS REFERENCE TO RELATED APPLICATIONS

This patent application claims the benefit of U.S. Provisional Application. No. 62/560,104, filed Sep. 18, 2017, entitled TRANSFER ASSEMBLY.

BACKGROUND OF THE INVENTION

1. Field of the Invention

The present invention relates generally to facilitating the passing of catheters through the cervical canal and more particularly to a transfer assembly that includes a specialized support element designed to prove comfort for the patient and concomitantly insuring proper positioning of cannula assemblies or catheters during insertion thereof.

2. Description of the Related Art

The introduction of a cannula through the human cervix to reach the uterus is a common practice in reproduction assisted techniques and office infertility and gynecology practices; including, for example, embryo transfer, intrauterine artificial insemination (IUI), sonohysterography, endometrial biopsy, IUD (intrauterine device) insertion, etc. In many instances it is difficult to direct an instrument through the cervical canal (from the external cervical hole to the internal cervical hole) with soft or rigid cannulas without hurting the canal causing pain, discomfort and bleeding. Heretofore, there has been no effective device that facilitates this procedure avoiding these detrimental effects.

SUMMARY OF THE INVENTION

In a broad aspect, the present invention is a sterile liquid transfer assembly for use with a catheter assembly. The sterile liquid transfer assembly includes a protective element and a carrier element. The protective element includes a pliable, hollow protective valve member having a pivot cutaway portion. A tubular member of the protective element depends from a surface of the hollow protective valve member. The protective valve member is configured to define a stop for limiting the insertion of the tubular member in a canal of a patient.

The carrier element includes an elongated transportation element; a handle; a valve mating member; and a flexible guide member. The elongated transportation element has a protective valve member stabilizing extension at a proximal end thereof. The handle is located at a distal end of the elongated transportation element. The valve mating member is constructed to cooperate with an inner volume of the hollow protective valve member. The valve mating member has a radial extension for cooperating with the pivot cutaway portion. The protective valve member stabilizing extension is constructed to be received in the tubular member during use. The thin, flexible guide wire has a guide wire distal end positioned at a distal end of the elongated transportation element at the handle. The guide wire extends through the elongated transportation element to provide stability to the protective valve element and the carrier element.

During use the sterile liquid transfer assembly is positioned within a patient so that the protective valve element is located at a specific, predefined position in the canal of the patient. Upon proper positioning, the carrier element is rotated to allow the carrier element to be removed. The protective valve element is maintained within the canal, its pliable characteristic providing comfort for the patient and concomitantly insuring proper positioning of the catheter and catheter guide during insertion thereof. The protective valve member and the valve mating member are constructed and arranged to have a complementary fit The principles of the present invention are particularly advantageous when the sterile liquid transfer assembly is embodied as an embryo transfer assembly. In such an instance, in a preferred embodiment, the protective element takes the form of a cone element, the protective valve member is a conical valve member, the catheter is specifically a cannula, the valve mating member takes the shape of an elongated bulb member, and the device is used in the uterus inner cervical canal. The present invention requires less time than presently used procedures, obviates the need for rigid catheters for passing through the cervical canal, and provides less harm to the embryos.

Applications are not limited however to embryo transfer. The sterile liquid transfer assembly may be used in other applications, including, but not limited to semen transfer, sterile water transfer, culture media transfer, etc. The advantages discussed above apply equally with respect to these other applications.

BRIEF DESCRIPTION OF THE DRAWINGS

The same elements or parts throughout the figures of the drawings are designated by the same reference characters, while equivalent elements bear a prime designation.

DETAILED DESCRIPTION OF THE INVENTION

Figure 1:
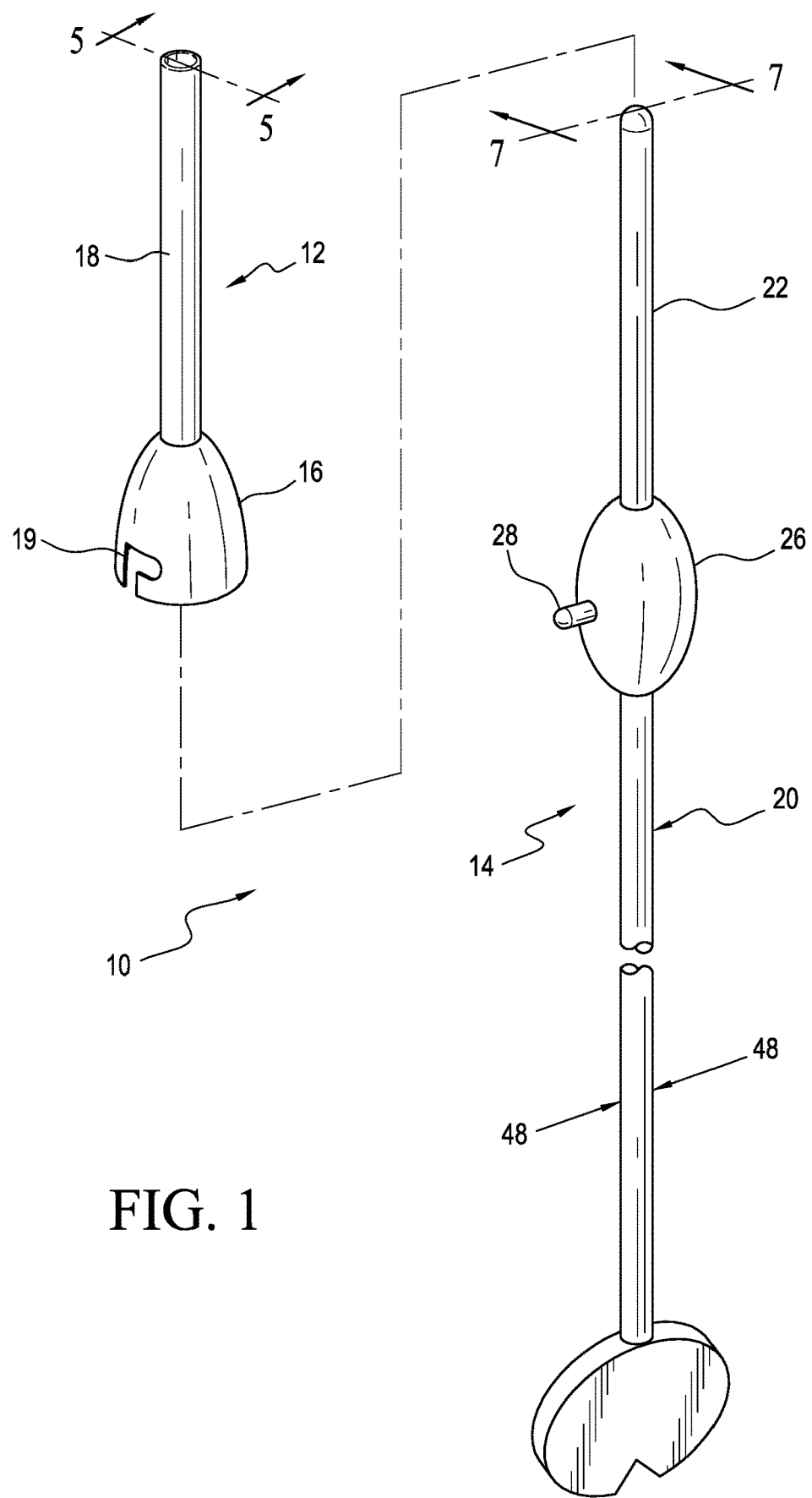
FIG. 1 is an exploded perspective view of the embryo transfer assembly of the present invention.

Referring now to the drawings and the characters of reference marked thereon, FIG. 1 illustrates a preferred embodiment of the sterile liquid transfer assembly embodied as an embryo transfer assembly, designated generally as 10, in accordance with the principles of the present invention. The embryo transfer assembly 10 includes a cone element, designated generally as 12, and a carrier element, designated generally as 14. The cone element 12 includes a pliable, hollow conical member 16; and, a tubular member 18. The pliable, hollow conical member 16 has a pivot cutaway portion 19. The tubular member 18 depends from an apex of the hollow conical member 16. The hollow conical member 16 is configured to define a stop for limiting the insertion of the tubular member 18 in a uterus inner cervical canal of a patient. The carrier element 14 includes an elongated transportation element 20 having a conical member stabilizing extension 22 at a proximal end thereof. A handle 24 is located at a distal end of the elongated transportation element 20. An elongated bulb member 26 is constructed to cooperate with an inner volume of the hollow conical member 16. The elongated bulb member 26 as a radial extension 28 for cooperating with the pivot cutaway portion 19. The conical member stabilizing extension 22 is constructed to be received in the tubular member 18 during use.

A thin, flexible guide wire 30 (see FIG. 7) has a guide wire distal end 32 positioned at a distal end of the elongated transportation element 20 at the handle 24. The guide wire 30 extends through the elongated transportation element 20 to provide stability to the cone element 12 and the carrier element 14.

Figure 2:
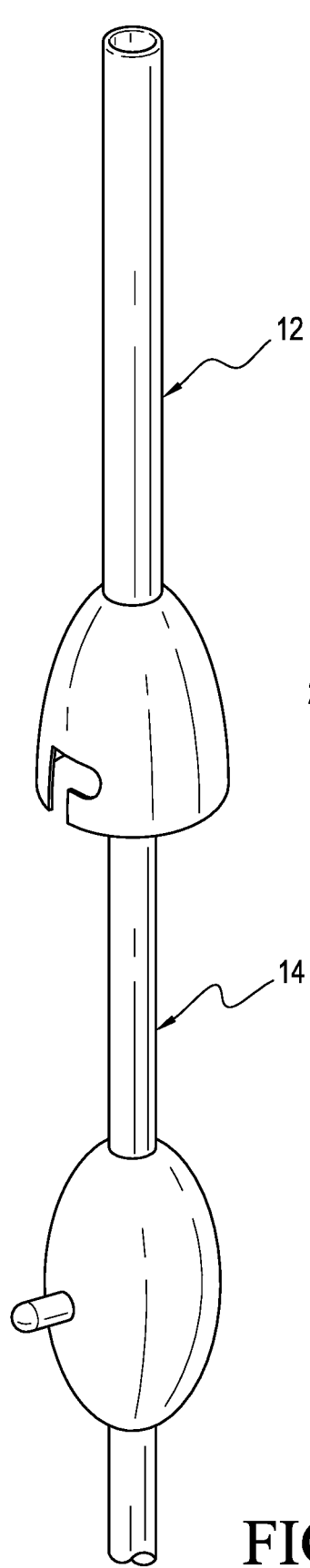
FIG. 2 illustrates an initial step of assembling the embryo transfer assembly for placement within the uterus inner cervical canal.
Figure 3:
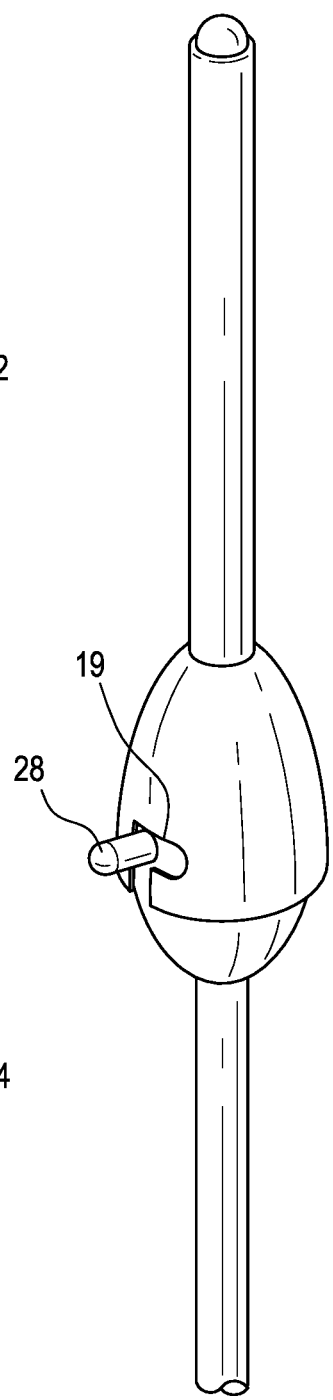
FIG. 3 illustrates a next step of assembling the embryo transfer assembly.
Figure 4:
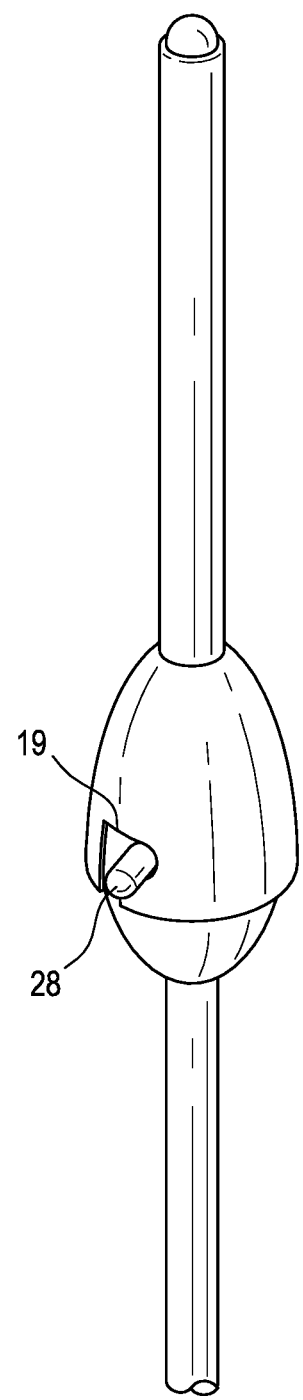
FIG. 4 illustrates a next step of assembling the embryo transfer assembly by rotating the elongated transportation element.

FIG. 2 illustrates an initial step of assembling the embryo transfer assembly for placement within the uterus inner cervical canal. The carrier element 14 is shown being introduced to the cone element 12. In FIG. 3 the radial extension 28 of the cone element 12 is shown being introduced into the cutaway portion 19. FIG. 4 shows relative rotation of the carrier element 14 and the cone element 12 so that the two elements are secured.

Figure 5:
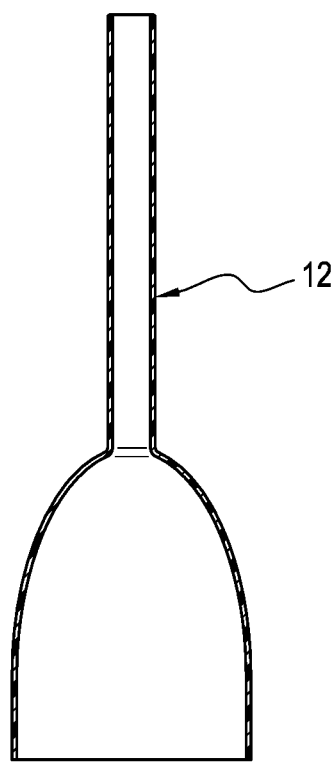
FIG. 5 is a view taken along line 5-5 of FIG. 1.
Figure 6:
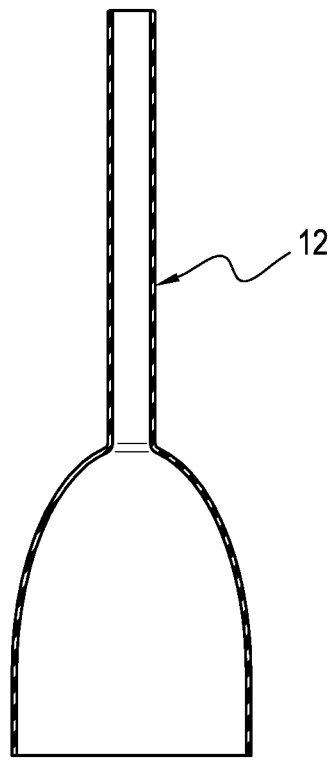
FIG. 6 shows a cone element of a different material than the FIG. 5 embodiment.

In FIG. 5 the cone element 12 is shown as plastic. In FIG. 6 the cone element 12 is shown as rubber latex.

Figure 7:
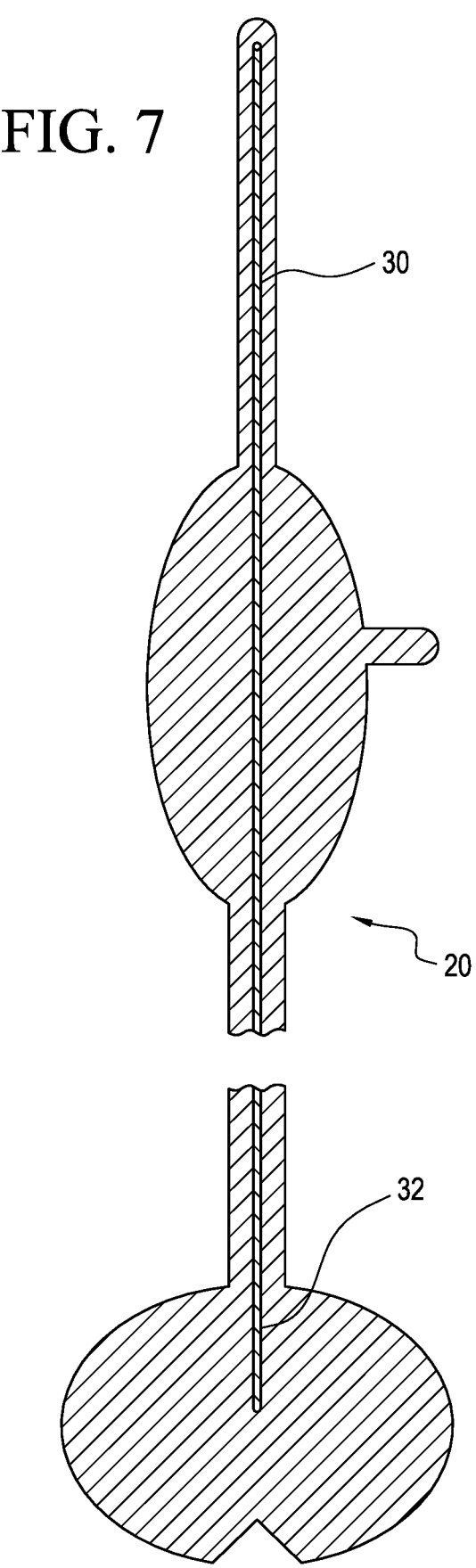
FIG. 7 is a view taken along line 7-7 of FIG. 1.

FIG. 7 shows how the guide wire 30 extends through the embryo transfer assembly 10. Although a thin, flexible guide wire 30 has been shown other suitable types of flexible guide members may be utilized, for example, flexible guide members formed of plastic.

Figures 8, 9:
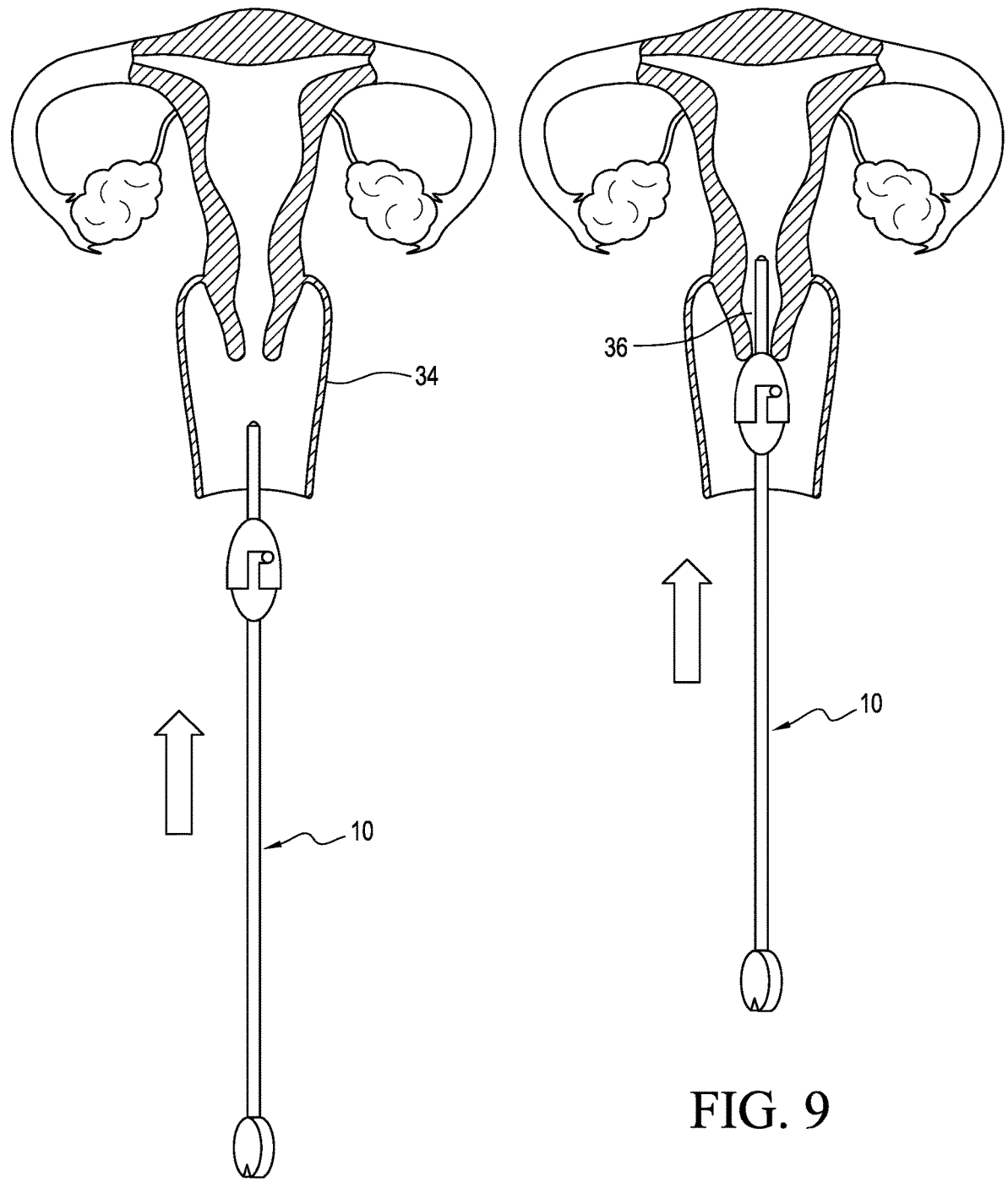
FIG. 8 is a schematic illustration showing the embryo transfer assembly being introduced within the vagina.
FIG. 9 shows the embryo transfer assembly at the entrance to the cervical canal.

Referring now to FIG. 8, the assembled embryo transfer assembly 10 is shown being introduced within the vagina 34. In FIG. 9, the embryo transfer assembly 10 is shown at the entrance to the cervical canal 36.

Figures 10, 11:
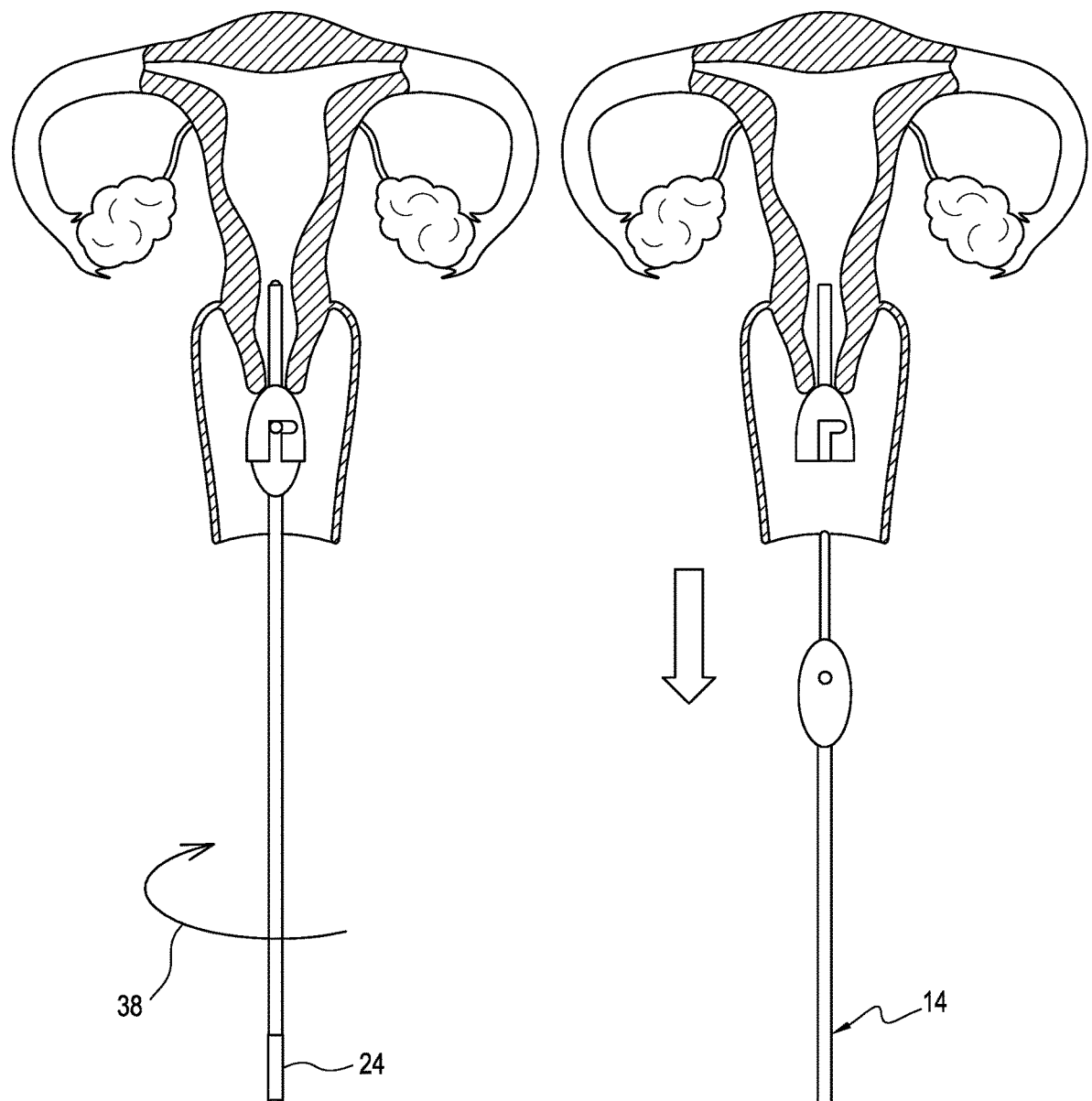
FIG. 10 illustrates the rotation of the handle to accommodate the release of the carrier element.
FIG. 11 shows the release of the carrier element to allow access for the cannula assembly.
Figures 12, 13:
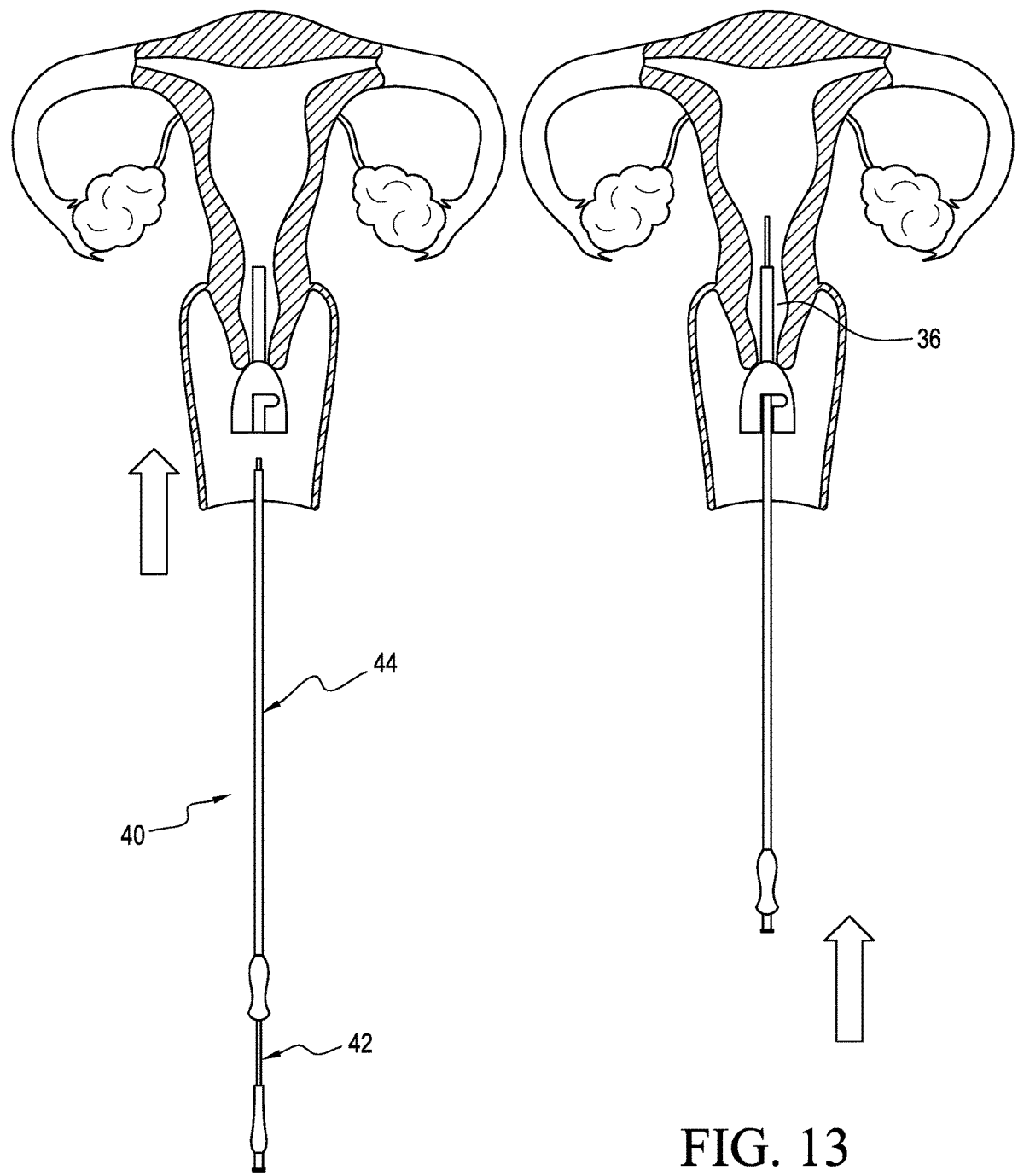
FIG. 12 shows the introduction of the cannula assembly to the cone assembly.
FIG. 13 illustrates the insertion of the cannula into the cervical canal.

Once positioned properly the handle 24 is rotated to accommodate the release of the carrier element 14, as shown by arrow 38. FIG. 11 illustrates the release of the carrier element 14 to allow access of a cannula assembly 40. FIG. 12 shows the introduction of the cannula assembly 40 which includes a cannula 42 and a cannula guide 44. In FIG. 13 the cannula 42, as guided by the cannula guide 44 is inserted into the cervical canal 36. Although the handle 24 is shown as being circular it can be of a variety of different shapes.

Figures 14, 15:
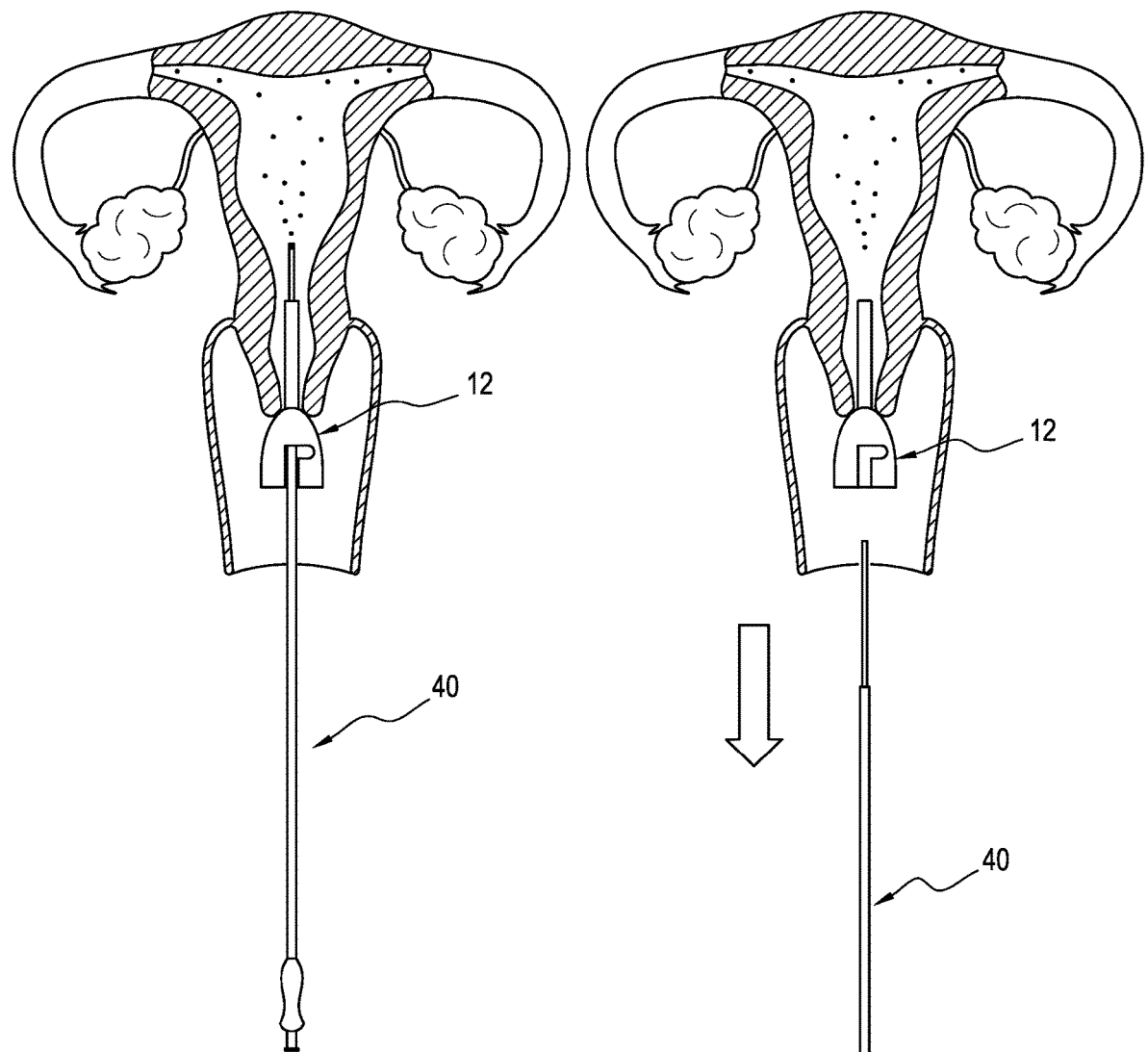
FIG. 14 shows the injection of embryos.
FIG. 15 illustrates the removal of the cannula assembly.
Figures 16, 17:
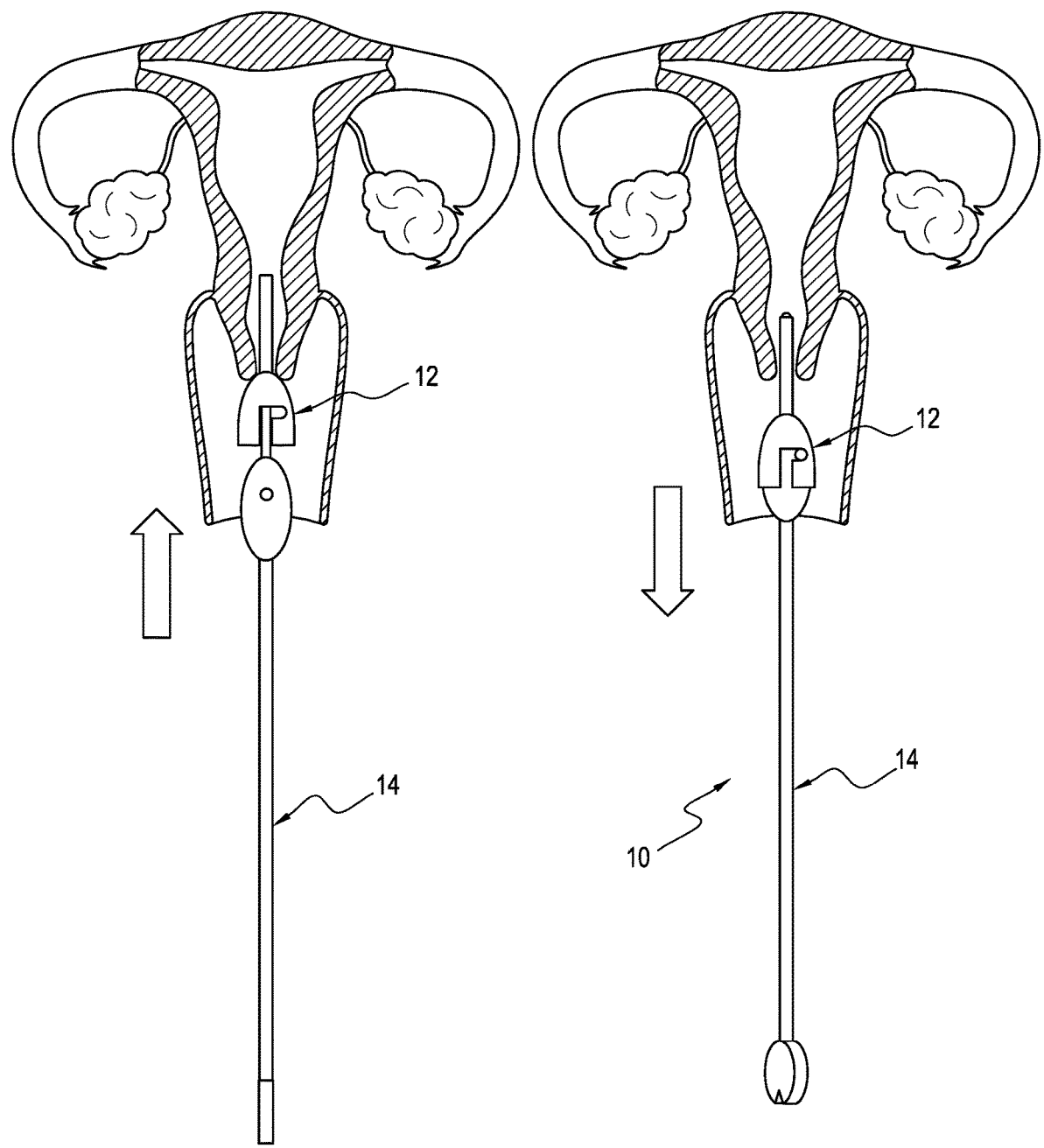
FIG. 16 illustrates reinsertion of the carrier element into the cone element.
FIG. 17 illustrates the removal of the embryo transfer assembly.

FIG. 14 illustrates the injection of embryos 46 through the cannula assembly 40 into the uterus inner cervical canal 36 of the patient. FIG. 15 illustrates the removal of the cannula assembly 40 after the injection of the embryos 46. After removal of the cannula assembly 40, as shown in FIG. 16, the carrier element 14 is reinserted into the cone element 12. This facilitates removal of the embryo transfer assembly 10, as shown in FIG. 17.

Although the present invention has been discussed specifically with respect to embryo transfer it has far-reaching applications to other reproduction assisted techniques and office infertility and gynecology practice. For example, it can be used for intrauterine artificial insemination (IUI), sonohysterography, endometrial biopsy, IUD (intrauterine device) insertion, etc. It can be used for various catheters. It reduces the amount of pain, discomfort, and bleeding.

Although the stop element for providing a stop for limiting the insertion of the tubular member in the uterus inner cervical canal has been described as a cone element with a conical member, the stop element can be of a variety of shapes that provide a comfortable positioning within the patient without altering its function.

Thus, the cone member may in some embodiments, be embodied as some other type of protective element. The conical member may have a different shape as a cone but still serve the function of a protective valve. The cannula may be of a variety of different catheters depending on the application. The elongated bulb member may be some other suitable type of valve mating member.

When the sterile liquid transfer assembly is embodied as an embryo transfer assembly the elongated transportation element 20 preferably has an outer diameter, denoted by arrows 48, in a range of about 35 to about 45 cm, preferably about 40 cm. The length of the stabilizing extension 22 is preferably in a range of about 2.5 to about 3.8 cm, preferably about 3.2 cm. the total length of elongated transportation element 20, including the handle 24 is about 24.4 cm. The handle 24 is about 20 cm long. The elongated bulb member 26 is about 3.2 cm long and has a diameter at its maximum cross-section of about 1.58 cm.

Other embodiments and configurations may be devised without departing from the spirit of the invention and the scope of the appended claims.

The invention claimed is:

1. A sterile liquid transfer assembly for use with a catheter assembly, comprising:
    a) a protective element, including:
        i. a pliable, hollow protective member having a pivot cutaway portion; and,
        ii. a tubular member depending from a surface of said hollow protective member, wherein said protective member is configured to define a stop for limiting an insertion of said tubular member in a canal of a patient;
    b) a carrier element, including;
        i. an elongated transportation element having a protective member stabilizing extension at a proximal end thereof, and said protective member stabilizing extension constructed to be received in said tubular member during use;
        ii. a handle located at a distal end of the elongated transportation element;
        iii. a mating member constructed to cooperate with an inner volume of the hollow protective member, said mating member having a radial extension for cooperating with the pivot cutaway portion;
        iv. a flexible guide member having a guide member distal end positioned at a distal end of the elongated transportation element at the handle, said guide member extending through said elongated transportation element to provide stability to the protective element and the carrier element,
    wherein during use the sterile liquid transfer assembly is configured to be positioned within the patient so that the protective element is located at a specific, pre-defined position in the canal of the patient, whereupon after proper positioning the carrier element is rotated to allow the carrier element to be removed, the protective element being maintained within the canal, providing comfort for the patient and concomitantly insuring proper positioning of a catheter and a catheter guide during the insertion thereof.

2. The sterile liquid transfer assembly of claim 1, wherein said protective member and said mating member are constructed and arranged to have a complementary fit.

3. The sterile liquid transfer assembly of claim 1, wherein said protective element comprises a cone element; and, said pliable, hollow protective member comprises a conical member.

4. The sterile liquid transfer assembly of claim 1, wherein said protective member is formed of a rubber material.

5. The sterile liquid transfer assembly of claim 1, wherein said protective member is formed of rubber latex material.

6. The sterile liquid transfer assembly of claim 1, wherein said protective element is formed of plastic material.

7. The sterile liquid transfer assembly of claim 1, further including a catheter assembly including a catheter guide and a catheter.

8. An embryo transfer assembly for use with a cannula assembly, comprising:
   a) a cone element, including:
      i. a pliable, hollow conical member having a pivot cutaway portion; and,
      ii. a tubular member depending from an apex of said hollow conical member, wherein said hollow conical member is configured to define a stop for limiting an insertion of said tubular member in a uterus inner cervical canal of a patient;
   b) a carrier element, including;
      i. an elongated transportation element having a conical member stabilizing extension at a proximal end thereof, and said conical member stabilizing extension constructed to be received in said tubular member during use;
      ii. a handle located at a distal end of the elongated transportation element;
      iii. an elongated bulb member constructed to cooperate with an inner volume of the hollow conical member, said elongated bulb member having a radial extension for cooperating with the pivot cutaway portion;
      iv. a flexible guide member having a guide member distal end positioned at a distal end of the elongated transportation element at the handle, said guide member extending through said elongated transportation element to provide stability to the cone element and the carrier element,
   wherein during use the embryo transfer assembly is configured to be positioned within the patient so that the cone element is located at a specific, pre-defined position in the uterus inner cervical canal of the patient, whereupon after proper positioning the carrier element is rotated to allow the carrier element to be removed, the cone element being maintained within the uterus inner cervical canal, providing comfort for the patient and concomitantly insuring proper positioning of a cannula and a cannula guide during the insertion thereof.

9. The embryo transfer assembly of claim 8, wherein said hollow conical member is formed of a rubber material.

10. The embryo transfer assembly of claim 8, wherein said hollow conical member is formed of rubber latex material.

11. The embryo transfer assembly of claim 8, wherein said carrier element is formed of plastic material.

12. The embryo transfer assembly of claim 8, further including a catheter assembly including a catheter guide and a catheter.

* * * * *